United States Patent [19]

Beard

[11] 4,031,228

[45] * June 21, 1977

[54] 5(6)-BENZENE RING SUBSTITUTED BENZIMIDAZOLE-2-CARBAMATE DERIVATIVES HAVING ANTI-PROTOZOAL ACTIVITY

[75] Inventor: Colin C. Beard, Palo Alto, Calif.

[73] Assignee: Syntex (U.S.A.) Inc., Palo Alto, Calif.

[ * ] Notice: The portion of the term of this patent subsequent to June 8, 1993, has been disclaimed.

[22] Filed: Mar. 22, 1976

[21] Appl. No.: 669,373

Related U.S. Application Data

[60] Continuation-in-part of Ser. No. 566,014, April 7, 1975, Pat. No. 3,962,437, which is a division of Ser. No. 371,365, June 19, 1973, Pat. No. 3,901,901.

[52] U.S. Cl. .................................. 424/270; 424/246
[51] Int. Cl.$^2$ ............... A61K 31/425; A61K 31/54
[58] Field of Search ............................ 424/246, 270

[56] References Cited

UNITED STATES PATENTS 3,962,437  6/1976  Beard ........................... 260/243 R Primary Examiner—Sam Rosen
Attorney, Agent, or Firm—Tom M. Moran; Joseph I. Hirsch

[57] ABSTRACT

Benzene ring substituted benzimidazole-2-carbamate derivatives represented by the formula:

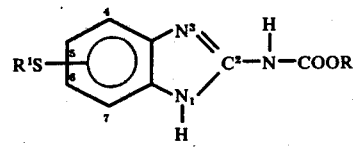

where R is a lower alkyl group having 1 to 4 carbon atoms; and $R^1$ is a fused, bicyclic heterocyclic ring moiety. The $R^1S$-substitution is at the 5(6)-position.

The compounds are useful as pesticides, particularly as anthelmintic and antifungal agents. The compounds are also useful as antiprotozoal agents, particularly against *Trichomonas vaginalis*.

18 Claims, No Drawings

1

5(6)-BENZENE RING SUBSTITUTED BENZIMIDAZOLE-2-CARBAMATE DERIVATIVES HAVING ANTI-PROTOZOAL ACTIVITY

REFERENCE TO PARENT APPLICATIONS

This is a continuation-in-part of application Ser. No. 566,014, filed Apr. 7, 1975, now U.S. Pat. No. 3,962,437, which, in turn, is a division of application Ser. No. 371,365, filed June 19, 1973, now U.S. Pat. No. 3,901,901.

FIELD OF THE INVENTION

This invention relates to novel chemical compounds. More particularly, this invention relates to novel anthelmintically active benzimidazole-2-carbamate derivatives wherein the benzene ring is substituted at the 5(6)-position.

BACKGROUND OF THE INVENTION

Anthelmintically active benzimidazole-2-carbamate derivatives either unsubstituted at the 5(6)-position or substituted with different substituents than those described and claimed herein are known in this art (for example, see U.S. Pat. Nos. 3,480,642; 3,573,321; 3,574,845; 3,578,676; and 3,595,870). Related fungicidal compounds are also shown in U.S. Pat. Nos. 2,933,504 and 3,010,968.

SUMMARY OF THE INVENTION

The novel benzene ring substituted benzimidazole-2-carbamate derivatives of the present invention can be represented by the following formula:

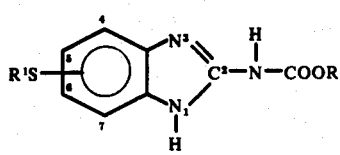

(I)

where R is a lower alkyl group having 1 to 4 carbon atoms; and $R^1$ is a fused, bicyclic heterocyclic ring moiety having 5 or 6 atoms in each ring, the rings having 2 common atoms one of which is a nitrogen atom, and the other of which is a carbon atom, the carbon atom being covalently bonded to the nitrogen atom, a hetero sulfur atom in each ring and the sulfur atom between the heterocyclic ring moiety and the benzimidazole nucleus. The $R^1S$-substitution is at the 5(6)-position.

The hydrogen on the nitrogen at the 1-position can be replaced with substituents which do not adversely affect the anthelmintic and/or antifungal properties of the basic compound, including acyl, carbalkoxy, carbamoyl, alkyl-substituted carbamoyl, etc., substituents.

As used in this specification and claims, the term "lower alkyl" refers to both straight and branched chain alkyl groups having a total of from 1 through 4 carbon atoms, and thus includes methyl, ethyl, n-propyl, isopropyl, n-butyl, isobutyl, and t-butyl. The term "fused, bicyclic heterocyclic ring" refers to both unsubstituted and substituted heterocyclic ring moieties having 5 or 6 atoms in each ring, the rings having 2 common atoms, one of which is a nitrogen atom, and the other of which is a carbon atom, the carbon atom being covalently bonded to the nitrogen atom, a hetero sulfur atom in each ring and the sulfur atom between the heterocyclic ring moiety and the benzimidazole nucleus, and includes both saturated and unsaturated heterocyclic rings. Exemplary fused, bicyclic heterocyclic rings expressed in radical form include, for example, 2,3,5,6,-tetrahydro-thiazolo[2,3-b]thiazol-7a-yl; 2,3-dihydro-thiazolo[2,3-b]thiazol-7a-yl; thiazolo [2,3-b]-thiazol-7a-yl; 2,3,5,6-tetrahydrothiazolo[2,3-b]-(1,3)-thiazin-8a-yl; 2,3,6,7-tetrahydro-(1,3)thiazino[2,3-b]-(1,3)-thiazin-9a-yl; and the like. The aforementioned fused, bicyclic heterocyclic ring can be substituted with one or more alkyl, such as methyl; aryl, such as phenyl; alkoxy, such as methoxy; or hydroxy radicals. The term "cycloalkyl" refers to cyclic hydrocarbon group having from 3 to 7 carbon atoms including, for example, cyclopropyl, cyclopentyl, cyclohexyl, and the like. The term "alkoxy" refers to the group having the formulae RO— wherein R is a lower alkyl, as defined above, and includes, for example, methoxy, ethoxy, propoxy, t-butoxy, and the like. The term "halo" refers to iodo, bromo, chloro, and fluoro radicals. The term "acyl" refers to acyl groups derived from carboxylic acids having from 1 to 6 carbon atoms, such as, for example, acetyl, propionyl, butyryl, valeryl, isovaleryl, hexanoyl, and the like.

Thus, the compounds of the present invention include those having the following formula:

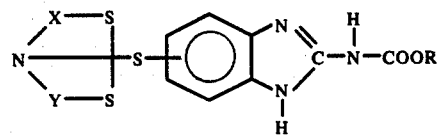

were R is as defined above; and X and Y are independently —C—C—, —C=C—, —C—C—C—, —C—C=C—, or —C=C—C—, or the substituted counterparts thereof, as set forth above.

The compounds of the present invention, and the non-toxic salts thereof formed with pharmaceutically acceptable inorganic or organic acids, possess activity against parasites in mammals, including both mature and immature parasitic forms. In particular, these compounds are found to exhibit high activity against tape worm infections of the intestinal tract of economically important animals, coupled with low systemic toxicity to the host animals. Such infections may be due to tapeworm parasites such as Hymenolepis nana, Dipylidium canium, Taenia saginata, Multiceps serialis, etc.

The compounds of the present invention are also useful as antifungal agents, particularly as systemic fungicides for controlling fungal diseases of plants of economic importance.

Where the compound has a basic moiety, the term "non-toxic salts" as used herein refers to those pharmaceutically acceptable salts of the compounds of this invention which do not adversely affect the antifungal or anthelmintic properties of the basic compound, such as those salts conventionally used in the art. Such non-toxic salts include, for example, salts of inorganic acids such as, for example, sulfuric, sulfonic, sulfamic, nitric, phosphoric, hydrochloric acids and the like, and salts of organic acids such as, for example, acetic, citric, lactic, palmitic, tartaric, succinic, maleic, benzoic acids and the like.

The amount of the compound to be administered will depend upon the actual compound utilized, and upon the weight of the animal being treated. In general, however, the daily dosage level will usually be between about 5 mg/kg and 100 mg/kg of body weight of the animal being treated. The active ingredient is administered to the animal by mixing it with the diet of the animal, as with a feed mix, or formulating it with a non-toxic carrier to give anthelmintic compositions. The carrier may be an orally ingestible container for the active ingredient such as, for example, a gelatin capsule, or it may be an excipient of the kind normally used in medicaments of this character, including maize starch, terra alba, lactose, sucrose, calcium phosphate, gelatin, stearic acid, agar, pectin or the like. Examples of suitable liquid carriers are peanut oil, sesame oil and water.

A wide variety of pharmaceutical forms can be employed in those cases wherein the medicament is not admixed with the feed. Thus, if a solid carrier is used, the compound can be administered in tablet or capsule form. If a liquid carrier is used, the medicament may be in the form of a soft gelatin capsule or in a liquid suspension.

The compounds of this invention, and the non-toxic salts thereof, as described below [particularly 5(6)-(2,3,5,6-tetrahydrothiazolo[2,3-b]thiazol-7a-ylthio)-2-carbomethoxy-aminobenzimidazole], also exhibit anti-protozoal activity against animal and human pathogens, for example against *Trichomonas vaginalis*. Thus, further aspects of this invention relate to methods for inhibiting the growth of protozoa by applying or administering to a host object containing, or subject to attack by, protozoa, an anti-protozoal effective amount of a compound of this invention, and compositions containing a compound of this invention in combination with a suitable carrier useful for such purpose. In pharmaceutical application, compositions for this aspect of the present invention may be solid, semi-solid or liquid in form such as tablets, capsules, powders, suppositories, liquid solutions, suspensions, creams, lotions, gels, ointments and the like. Pharmaceutically acceptable non-toxic carriers, or excipients normally employed for solid formulations include tricalcium phosphate, calcium carbonate, kaolin, bentonite, talcum, gelatin, lactose, starch and the like; for semi-solid formulations there may be mentioned, for example, polyalkylene gylcols, vaseline, petrolatum and other cream bases; for liquid formulations there may be mentioned, for example, water, oils of vegetable origin and low boiling solvents such as isopropanol, hydrogenated naphthalenes and the like. Such pharmaceutical compositions may be subjected to conventional pharmaceutical expedients such as sterilization and may contain conventional pharmaceutical additives such as preservatives, stabilizing agents, emulsifying agents, salts for the adjustment of osmotic pressure and buffers. The compositions may also contain other therapeutically active materials. The pharmaceutical compositions typically comprise a pharmaceutically acceptable, non-toxic carrier in combination with one or more compounds represented by Formula (I) in an amount effective for anti-protozoal relief. For example, in a topical formulation the amount of active ingredient may carry from about 0.1% by weight (%w) to about 10%w of the total pharmaceutical formulation, while other formulations may have from 5%w to 95%w or more active ingredient. Preferably such pharmaceutical compositions are formulated in unit dosage form to facilitate administration (unit dosage being the amount of active ingredients administered on one occasion). In this aspect of the present invention, the subject compounds and compositions may be administered to humans and animals by conventional methods, e.g. topically, orally, parenterally and the like. "Topical" administration includes intravaginal application while parenteral administration includes intramuscular as well as subcutaneous and intravenous injection. Topical application is the preferred method of administration in pharmaceutical applications. For such treatment, an area having an existing protozoal growth, or to be protected against attack by protozoa, may be treated with the subject compounds or compositions by, for example, dusting, sprinkling, spraying, rinsing, brushing, dipping, smearing, coating, impregnating and the like.

The exact regimen for pharmaceutical administration of the compounds and compositions disclosed herein will necessarily be dependent upon the needs of the individual subject being treated, the type of treatment, e.g. whether preventative or curative, the type of organism involved and, of course, the judgement of the attending practitioner. In general, for systemic (e.g. oral or parenteral) administration it is expedient to administer the active ingredient in amounts of between about 1 and 100 mg/kg body weight per day (preferably between about 5 and 50 mg/kg body weight per day) preferably distributed over several applications (e.g. in three individual doses) in order to achieve effective results. For localized (e.g. topical) administration, however, proportionately less of the active ingredient is required.

The 5(6) -substituted compounds of the present invention can be prepared from benzene starting compounds having nitro and amino or acylamino (for example, acetamido) substituents at adjacent positions on the benzene nucleus (e.g., the 1- and 2-positions), and a displaceable moiety, for example, a chloro substituent at the 4- or 5-position of the benzene nucleus (i.e., at what will be the 5(6)-position of the benzimidazole compound to be prepared). Such a benzene starting material is reacted with a heterocyclic mercaptan to give the corresponding 4- or 5-fused, bicyclic heterocyclicthio benzene derivative. If applicable, the acylamino group is converted to an amino group. The nitro group is reduced to an amino group to afford a benzene derivative having amino groups at the 1- and 2-position. The 1,2-diamino compound is then reacted with a 1,3-bis-(alkoxy-carbonyl)-S-alkyl isothiourea to give the corresponding 5(6)-fused, bicyclic heterocyclicthio-benzimidazole-2-carbamate compound of the present invention.

The fused, bicyclic heterocyclicthio compounds of the present invention can also be prepared by treating a suitable starting material having a thiocyanato group at the 4- or 5-position with sodium borohydride to form the corresponding mercaptide, reacting the mercaptide with an appropriate fused, bicyclic heterocyclic halide salt, converting the resultant compound to the corresponding 1,2-diamino-5(6)-fused, bicyclic heterocyclicthiobenzene compound, and reacting the latter compound with a 1,3-bis(alkoxy-carbonyl)-S-alkyl-isothiourea to give the corresponding 5(6)-fused, bicyclic heterocyclicthio-benzimidazole-2-carbamate derivative.

A suitable starting material is 1-acetamido-2-nitro-4-thiocyanatobenzene which can be prepared according to the method of F. Challenger and A. T. Peters, J. Chem. Soc., 1364 (1928). Other suitable starting materials include, for example, 1-amino-2-nitro-4-thiocyanatobenzene, 2-amino-4-chloro-1-nitrobenzene, and 2-acetamido-4-chloro-1-nitrobenzene.

Conversion of the thiocyanato group of the 1-acetamido-2-nitro-4-thiocyanatobenzene (or 1-amino-2-nitro-4-thiocyanatobenzene) starting material to a heterocyclicthio substituent can be affected by treatment of either of the aforementioned 4-thiocyanatobenzene starting materials, at room temperature, with sodium borohydride in dimethylformamide for about ¼ to about 2 hours, followed by treatment with a fused, bicyclic heterocyclic halide salt, such as, for example, 2,3,5,6-tetrahydrothiazolo-[2,3-b]-thiazolium chloride, and the like, in dimethylformamide, dimethylacetamide, quinoline, pyridine, or an alcoholic medium, such as methanol or ethanol. This latter reaction is conducted at a temperature from about 10° C. to about 150° C., generally at about room temperature if feasible, for about ½ to 12 hours using an excess of the halide reactant. The reaction is preferably conducted in dimethylformamide. Alternatively, the mercaptide intermediate can be generated with other bases instead of sodium borohydride.

Conversion of an acylamino group, for example, an acetamido group, to an amino group can be effected by treating the acylamino group-containing compound with a strong base, such as sodium hydroxide, potassium hydroxide, potassium carbonate, or sodium carbonate in aqueous methanol at about 20° C. to about 100° C. for about ¼ hour to about 24 hours.

Reduction of the nitro group to an amino group can be effected by treating a nitro-group containing compound with iron and a ferrous salt, such as ferrous sulfate or ferrous chloride, or zinc powder, in aqueous methanol or acetic acid at reflux under neutral conditions for about 1 to about 20 hours. It is desirable to add the metal powder in distinct portions, as opposed to all at one time.

The diamino compounds resulting from reduction of the nitro group in the starting compound to an amino group, and, if necessary, conversion of the acylamino group to an amino group, are converted to the corresponding benzimidazole-2-carbamate compounds by reacting the diamino compound with a 1,3-bis(alkoxycarbonyl)-S-alkyl-isothiourea, for example, 1,3-bis(-methoxycarbonyl)-S-methyl-isothiourea or 1,3-bis-(ethoxycarbonyl)-S-methyl-isothiourea, in an aqueous alcoholic medium, for example, aqueous methanol or aqueous ethanol, at from about room temperature to the reflux temperature of the reaction medium for about ½ to about 6 hours. The reaction medium is preferably made acidic to a pH of about 4–6 with, for example, a sufficient amount (e.g., 1–2 moles) of acetic acid. About 1–2 moles. generally about 1.1 moles, of the isothiourea reactant are utilized per mole of the diamino compound.

When 2-amino-4-chloro-1-nitrobenzene or 2-acetamido-4-chloro-1-nitrobenzene is utilized as a starting material, it can be converted to the corresponding heterocyclicthio compound, by the reaction thereof with an appropriate heterocyclic mercaptan, such as 4,5-dihydro-2-mercaptothiazole, and the like, in an inert solvent, such as dimethylformamide, ethanol, or methanol, in the presence of a suitable inorganic base, such as potassium hydroxide, potassium carbonate, sodium carbonate, sodium hydroxide or sodium hydride. Typically, this reaction is conducted at a temperature from about 20° C. to about 150° C. (i.e., to about the reflux temperature of the solvent material) for about ½ to about 6 hours, using an excess (2–3 moles) of the mercaptan reactant. If 2-acetamido-4-chloro-1-nitrobenzene is utilized as the starting material, the acetamido group can be converted to an amino group as described above. With either case, the nitro group is reduced to an amino group. The resultant 1,2-diamino compound is treated, as described above, to give the corresponding 5(6)-fused, bicyclic heterocyclicthio-benzimidazole-2-carbamate compounds of this invention.

In each of the process steps, described, herein above and below, unless otherwise indicated, the respective intermediate products are preferably separated from the reaction mixture and purified prior to their use as starting materials for the next step in the process. Such separation and purification can be effected by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation as will be apparent to those skilled in this art.

Particular compounds falling within the scope of the present invention can be prepared by selecting an appropriate starting material, for example, from those referred to above, and then selecting particular reaction step or steps, as for example described above, to give the compound desired. Particular reaction step or steps may be conducted in a different order from that specified above since, in certain instances, the particular sequence of steps may not be critical. For example, the acetamido group of a 1-acetamido-2-nitro-4-thiocyanatobenzene can be converted to an amino group before the reaction of such compound with a heterocyclic halide salt or the starting material can be reacted with the heterocyclic halide salt and then the acetamido group converted to the corresponding amino group. In view of this disclosure, the preparation of particular compounds, including compounds falling within the scope of the present invention but not particularly described in the specification, and the various sequences of reaction steps which can be utilized to prepare such compounds, will be apparent to those skilled in this art.

Exemplary of the compounds of the present invention, as represented by the structural formula above, are the following illustrative compounds:

5(6)-(2,3,5,6-tetrahydrothiazolo[2,3-b]thiazol-7a-ylthio)-2-carbomethoxyaminobenzimidazole;
5(6)-(2,3-dihydrothiazolo[2,3-b]thiazol-7a-ylthio)-2-carbomethoxyaminobenzimidazole;
5(6)-(thiazolo[2,3-b]thiazol-7a-ylthio)-2-carbomethoxy-aminobenzimidazole;
5(6)-(2,3,5,6-tetrahydrothiazolo[2,3-b]-(1,3)-thiazin-8a-ylthio)-2-carbomethoxyaminobenzimidazole;
5(6)-(5,6-dihydrothiazolo[2,3-b]-(1,3)-thiazin-8a-ylthio)-2-carbomethoxyaminobenzimidazole;
5(6)-(2,3,6,7-tetrahydro(1,3)thiazino[2,3-b]-(1,3)-thiazin-9a-ylthio)-2-carbomethoxyaminobenzimidazole;
5(6)-(2,3,5,6-tetrahydrothiazolo[2,3-b]thiazol-7a-ylthio)-2-carboethoxyaminobenzimidazole;
5(6)-(2,3-dihydrothiazolo[2,3-b]thiazol-7a-ylthio)-2-carboethoxyaminobenzimidazole;
5(6)-(thiazolo[2,3-b]thiazol-7a-ylthio)-2-carboethoxy-aminobenzimidazole;

5(6)-tetrahydrothiazolo[2,3-b]-(1,3)-thiazin-8a-ylthio)-2-carboethoxyaminobenzimidazole;
5(6)-(5,6-dihydrothiazolo[2,3-b]-(1,3)-thiazin-8a-ylthio)-2-carboethoxyaminobenzimidazole;
5(6)-(2,3,6,7-tetrahydro(1,3)thiazino[2,3-b]-(1,3)-thiazin-9a-ylthio)-2-carboethoxyaminobenzimidazole;
5(6)-(2,3,5,6-tetrahydrothiazolo[2,3-b]thiazol-7a-ylthio)-2-carbopropoxyaminobenzimidazole;
5(6)-(2,3-dihydrothiazolo[2,3-b]thiazol-7a-ylthio)-2-carbopropoxyaminobenzimidazole;
5(6)-(thiazolo[2,3-b]thiazol-7a-ylthio)-2-carbopropoxy-aminobenzimidazole;
5(6)-(2,3,5,6-tetrahydrothiazolo[2,3-b]-(1,3)-thiazin-8a-ylthio)-2-carbopropoxyaminobenzimidazole;
5(6)-(5,6-dihydrothiazolo[2,3-b]-(1,3)-thiazin-8a-ylthio)-2-carbopropoxyaminobenzimidazole;
5(6)-(2,3,6,7-tetrahydro(1,3)thiazino[2,3-b]-(1,3)-thiazin-9a-ylthio)-2-carbopropoxyaminobenzimidazole;
5(6)-(2,3,5,6-tetrahydrothiazolo[2,3-b]thiazol-7a-ylthio)-2-carbobutoxyaminobenzimidazole;
5(6)-(2,3-dihydrothiazolo[2,3-b]thiazol-7a-ylthio)-2-carbobutoxyaminobenzimidazole;
5(6)-(thiazolo[2,3-b]thiazol-7a-ylthio)-2-carbobutoxy-aminobenzimidazole;
5(6)-(2,3,5,6-tetrahydrothiazolo[2,3b]-(1,3)-thiazin-8a-ylthio)-2-carbobutoxyaminobenzimidazole;
5(6)-(5,6-dihydrothiazolo[2,3-b]-(1,3)-thiazin-8a-ylthio)-2-carbobutoxyaminobenzimidazole; and
5(6)-(2,3,6,7-tetrahydro(1,3)thiazino[2,3-b]-(1,3)-thiazin-9a-ylthio)-2-carbobutoxyaminobenzimidazole.

Of the compounds listed above, 5(6)-(2,3,5,6-tetrahydrothiazolo[2,3-b]thiazol-7a-ylthio-2-carbomethoxyaminobenzimidazole is presently preferred because it has shown substantial and quite specific activity against *Hymenolepis nana* at extremely low concentrations. Thee compound is, thusly, an anthelmintic agent specifically adapted for treatment of tapeworm infections of the intestinal tract of economically important animals.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

PREPARATION 1

175 G. of S-methyl isothiouronium sulfate in 1 liter of water is cooled to 0° C. and 162.5 g. of methylchloroformate added, followed by the addition of a solution of 250 g. of potassium hydroxide in 750 ml. water at 0° to 5° C. The crude product is extracted into benzene, the benzene dried and evaporated, and the residue recrystallized from methanol. 1,3-bis(methoxycarbonyl)-S-methyl isothiourea is thus obtained.

In a similar manner, substituting ethylchloroformate, propylchloroformate and butylchloroformate for the methylchloroformate, 1,3-bis(ethoxycarbonyl)-S-methyl isothiourea, 1,3-bis(propoxycarbonyl)-S-methyl isothiourea, and 1,3-bis-(butoxycarbonyl)-S-methyl isothiourea are, respectively, prepared.

PREPARATION 2

A mixture of 12 g. of thiazolidine-2-thione, and 16 g. of 1-bromo-3-chloro propane in 100 ml. of acetonitrile is refluxed for 12 hours, cooled and the product removed by filtration. Recrystallization from ethanol gives 2,3,5,6-tetrahydrothiazolo[2,3-b]-(1,3)-thiazinium bromide.

PREPARATION 3

A mixture of 66.5 g. of tetrahydro-1,3-thiazin-2-thione and 83 g. of 1-bromo-3-chloropropane in 200 ml. of ethanol is refluxed for 24 hours. The solvent is removed under vacuum and the residue triturated with ether, then acetone. The product is recrystallized from ethanol yielding 2,3,6,7-tetrahydro-(1,3)-thiazino-[2,3-b]-(1,3)-thiazinium bromide.

PREPARATION 4

Thiazolo [2,3-b]-thiazolium chloride and thiazolo[2,3-b]-thiazolium bromide are prepared according to the procedure of Bradsher et al, Tetrahedron Letters No. 22, pp. 1723–1725 (1965) using chloroacetaldehyde or bromoacetaldehyde acetal, respectively, in place of the haloacetone or the phenacyl halide.

PREPARATIONS 5 AND 6

2-Mercapto-thiazole is reacted with 1-bromo-2-chloroethane or 1-bromo-3-chloropropane to afford, respectively, 2,3-dihydrothiazolo[2,3-b]thiazolium halide and 5,6-dihydrothiazolo[2,3-b]-(1,3)-thiazinium halide. Alternatively, these compounds can be prepared according to Bradsher et al, supra, using chloroacetaldehyde or bromoacetaldehyde acetal and the requisite heterocyclic starting material.

EXAMPLE I

A mixture of 121 g. of 2-amino-4-chloro-1-nitrobenzene, 208 g. of thiazolidine-2-thione, 242 g. of potassium carbonate and 1 liter of dimethylformamide is stirred at 90° to 100° C. for 8 hours, cooled and drowned into water. The insoluble material is washed with water and a little methanol, and then treated with boiling chloroform, cooled, and the product filtered off. Re-treatment with boiling chloroform and a similar treatment with boiling methanol gives 2-amino-4-[2,3,5,6-tetrahydrothiazolo[2,3-b]-thiazol-7a-yl]-1-nitrobenzene. Recrystallization may be effected from acetic acid if desired.

60 g. of 2-amino-4-[2,3,5,6-tetrahydrothiazolo[2,3-b]-thiazol-7a-yl]-1-nitrobenzene is suspended in 3 liters of methanol. 60 G. of iron powder and a solution of 30 g. of ferrous sulfate in 600 ml. of water are added. The mixture is stirred under gentle reflux for approximately 15 hours, during which period three further 60 g. portions of iron are added, and after which essentially no starting material remains. The mixture is filtered and the filtrate is concentrated under vacuum, the residue is dissolved in a warm mixture of 1 liter of ethanol and 1 liter of water, and re-filtered. 40 G. of 1,3-bis-methoxycarbonyl-S-methyl-isothiourea and 15 ml. of acetic acid are added. The mixture is refluxed gently for 4 hours, cooled and the product filtered off and washed with aqueous ethanol, then methanol to afford 5(6)-(2,3,5,6-tetrahydrothiazolo[2,3b]thiazol-7a-ylthio)-2-carbomethoxyamino-benzimidazole. Recrystallization may be effected from aqueous acetic acid if desired.

In a similar manner substituting 1,3-bis(ethoxycarbonyl)-S-methyl isothiourea, 1,3-bis(propoxycarbonyl)-S-methyl isothiourea, and 1,3-bis(butoxycarbonyl)-S-methyl isothiourea for the 1,3-bis(methoxycarbonyl)-S-methyl isothiourea, the corresponding 5(6)-[2,3,5,6-tetrahydrothiazolo-[2,3-b]-thiazol-7a-ylthio]-2-carbalkoxyamino-benzimidazole compounds are prepared, where R is ethyl, propyl and butyl, respectively.

EXAMPLE II

A solution of 2.37 g. of 1-acetamido-2-nitro-4-thiocyanatobenzene in 15 ml. dimethylformamide is treated under nitrogen with 0.38 g. of sodium borohydride at 20°–30° C. After 1 hour, 5 ml. of acetone is added followed, 1 hour later, by 6 g. of 2,3,5,6-tetrahydrothiazolo-[2,3-b]-thiazolium-chloride [See Seto et al, Bull. Chem Soc. Japan 36(6),730–4 (1963); Chemical Abstracts 59, 7509(b)]. The mixture is stirred overnight at 20°–30° (under nitrogen) then treated with water. The crude product is filtered off and purified by recrystallization from methanol-chloroform with charcoal treatment, yielding 1-acetamido-2-nitro-4-(2,3,5,6-tetrahydrothiazole-[2,3-b]thiazol-7a-ylthio)-benzene.

0.55 G. of the above product is treated with a mixture of 2 ml. of 5 N aqueous sodium hydroxide and 20 ml. of methanol on the steam bath for 15–20 minutes. The mixture is diluted with water and filtered, yielding 1-amino-2-nitro-4-(2,3,5,6-tetrahydrothiazolo-[2,3-b]-thiazol-7a-ylthio)benzene. This is treated with 0.6 g. of iron powder and 0.3 g. of ferrous sulfate in 25 ml. water, and 100 ml. methanol. The mixture is refluxed for 5 hours, during which time an additional 0.6 g. of iron powder is added, filtered and the filtrate concentrated under vacuum. The residue is dissolved in a mixture of 10 ml. ethanol and 10 ml. water, filtered from traces of iron residues and treated with 0.32 g. of 1,3-bis-methoxycarbonyl-S-methyl isothiourea and 0.1 ml. acetic acid at reflux for 3 hours to afford 5(6)-(2,3,5,6-tetrahydrothiazolo[2,3-b]thiazol-7a-ylthio)-2-carbomethoxyamino-benzimidazole which is filtered off.

Using the reactants set forth in the last paragraph of Example I according to the procedure of this Example, the corresponding 5(6)-[2,3,5,6-tetrahydrothiazolo[2,3-b]-thiazol-7a-ylthio]2-carbalkoxyaminobenzimidazole compounds are prepared where R is ethyl, propyl or butyl.

EXAMPLE III

In a similar manner to the procedure of Example II, using 2,3-dihydrothiazolo[2,3-b]thiazolium bromide in place of the 2,3,5,6-tetrahydrothiazolo[2,3-b]thiazolium chloride, the corresponding 5(6)-(2,3-dihydrothiazolo[2,3-b]thiazol-7a-ylthio)-2-carbalkoxyaminobenzimidazole compounds are prepared, where R is methyl, ethyl, propyl or butyl.

EXAMPLE IV

In a similar manner to the procedure of Example II, using thiazolo[2,3-b]thiazolium chloride in place of the 2,3,5,6-tetrahydro-thiazolo[2,3-b]thiazolium chloride, the corresponding 5(6)-(thiazolo[2,3-b]thiazol-7a-ylthio)-2-carbalkoxyaminobenzimidazole compounds are prepared, where R is methyl, ethyl, propyl or butyl.

EXAMPLE V

In a similar manner to the procedure of Example II, using 2,3,5,6-tetrahydrothiazolo[2,3-b]-(1,3)-thiazinium bromide in placed of the 2,3,5,6-tetrahydrothiazolo[2,3-b]-thiazolium chloride, the corresponding 5(6)-(2,3,5,6-tetrahydrothiazolo[2,3-b]-(1,3)-thiazinium-8a-ylthio)-2-carbalkoxyaminobenzimidazole compounds are prepared, where R is methyl, ethyl, propyl or butyl.

EXAMPLE VI

In a similar manner to the procedure of Example II, using 2,3,6,7-tetrahydro-(1,3)-thiazino[2,3-b]-(1,3)-thiazinium bromide in place of the 2,3,5,6-tetrahydrothiazolo [2,3-b]thiazolium chloride, the corresponding 5(6)-(2,3,6,7-tetrahydro-(1,3)thiazino[2,3-b]-(1,3)-thiazin-9a-ylthio) 2-carbalkoxyaminobenzimidazole compounds are prepared, where R is methyl, ethyl, propyl, or butyl.

EXAMPLE VII

In a similar manner to the procedure of Example II, using 5(6)-dihydrothiazolo[2,3-b]-(1,3)-thiazinium bromide in place of the 2,3,5,6-tetrahydrothiazolo[2,3-b]thiazolium chloride the corresponding 5(6)-(5,6-dihydrothiazolo[2,3-b]-(1,3)-thiazin-8a-ylthio)-2-carbalkoxyaminobenzimidazole compounds are prepared, where R is methyl, ethyl, propyl or butyl.

EXAMPLE VIII 0.37 G. of 5(6)-(2,3,5,6-tetrahydrothiazolo[2,3-b]thiazol-7a-ylthio)-2-carbomethoxyaminobenzimidazole was suspended in 50 ml. of tetrahydrofuran. 0.25 Mls. of n-butyl isocyanate was added at 20°–25° C. After ~15 minutes, the mixture became homogenous, and was left for 15 hours, then filtered and the solvent removed under vacuum at 20°–25° C. The residue was triturated with acetone and the product filtered off to afford 1-(n-butylcarbamoyl)-5(6)-(2,3,5,6-tetrahydrothiazolo-[2,3-b]thiazol-7a-ylthio)-2-carbomethoxyaminobenzimidazole (m.p. 150° C dec.).

In certain of the Examples above, specific reaction sequences have been extended, in a general sense, to the preparation of other similar and related compounds. It should be understood, however, that with respect to any compound which has been prepared by the extension of a specific reaction sequence, it may be necessary or desirable to utilize solvents, reaction media, recrystallization media, reaction times or temperatures, etc., other than the ones given in the specific reaction sequence upon which such extension is based. Additionally, the specific reaction sequence or manner in which particular compounds are to be prepared will depend, inter alia, upon the availability of the necessary starting materials, or the ease in which the desired starting materials can be prepared, and the reactivity thereof. These variations are deemed to be within the skill of those working in this art and will be apparent from a consideration of the particular reactants utilized and/or particular compound desired to be produced.

EXAMPLE IX

5(6)-(2,3,5,6-Tetrahydrothiazolo[2,3-b]thiazol-7a-ylthio)-2-carbomethoxyaminobenzimidazole was tested four times against growths of *Trichomonas vaginalis* and was found to have a minimum inhibitory concentration of 10, 30, 30 and 30 µg/ml (corresponding to 10, 30, 30 and 30 ppm), respectively.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A method for inhibiting the growth of protozoa which comprises administering to a host object containing or subject to attach by protozoa, an anti-protozal effective amount of a compound represented by the formula:

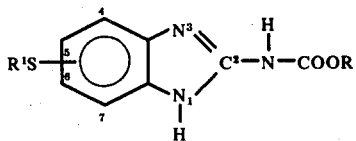

where R is a lower alkyl group having 1 to 4 carbon atoms; $R^1$ is a fused, bicyclic heterocyclic ring moiety having 5 or 6 atoms in each ring, the rings having 2 common atoms one of which is a nitrogen atom, and the other of which is a carbon atom, the carbon atom being covalently bonded to the nitrogen atom, a hetero sulfur atom in each ring and the sulfur atom between the heterocyclic ring moiety and the benzimidazole nucleus; the $R^1S$-substitution being at the 5(6)-position; or a pharmaceutically acceptable salt thereof.

2. The method of claim 1 wherein at least one of the member rings of said fused, bicyclic heterocyclic ring moiety of said compound is unsaturated.

3. The method of claim 1 wherein at least one of the member rings of said fused, bicyclic heterocyclic ring moiety of said compound is substituted with one or more alkyl, aryl, alkoxy or hydroxy radicals.

4. The method of claim 1 wherein said fused, bicyclic heterocyclic ring moiety of said compound is selected from the group consisting of 2,3,5,6-tetrahydrothiazolo[2,3-b]-thiazol-7a-yl; 2,3-dihydrothiazolo[2,3-b]thiazol-7a-yl; thiazolo[2,3-b]thiazol-7a-yl; 2,3,5,6-tetrahydrothiazolo-[2,3-b]-(1,3)-thiazin-8a-yl; and 2,3,6,7-tetrahydro-(1,3)-thiazino[2,3-b]-(1,3)thiazin-9a-yl.

5. The method of claim 1 wherein $R^1$ is 2,3,5,6-tetrahydrothiazolo[2,3-b]thiazol-7a-yl.

6. The method of claim 1 wherein said protozoa is Trichomonas vaginalis.

7. The method of claim 1 wherein said compound is 5(6)-(2,3,5,6-tetrahydrothiazolo[2,3-b]thiazol-7a-ylthio)-2-carbomethoxyaminobenzimidazole.

8. The method of claim 7 wherein said protozoa is Trichomonas vaginalis.

9. The method of claim 1 wherein the hydrogen on the nitrogen at the 1-position is replaced with acyl having 1 to 6 carbon atoms, carbalkoxy having 2 to 7 carbon atoms, carbamoyl, or alkylcarbamoyl wherein the alkyl portion thereof has 1 to 4 carbon atoms.

10. A composition for inhibiting the growth of protozoa which comprises a pharmaceutically acceptable non-toxic carrier and an anti-protozal effective amount of a compound represented by the formula:

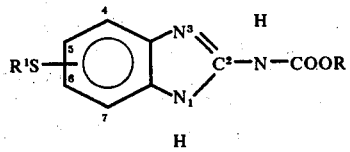

where R is a lower alkyl group having 1 to 4 carbon atoms; $R^1$ is a fused, bicyclic heterocyclic ring moiety having 5 or 6 atoms in each ring, the rings having 2 common atoms one of which is a nitrogen atom, and the other of which is a carbon atom, the carbon atom being covalently bonded to the nitrogen atom, a hetero sulfur atom in each ring and the sulfur atom between the heterocyclic ring moiety and the benzimidazole nucleus; the $R^1S$-substitution being at the 5(6)-position; or a pharmaceutically acceptable salt thereof.

11. The composition of claim 10 wherein at least one of the member rings of said fused, bicyclic heterocyclic ring moiety of said compound is unsaturated.

12. The composition of claim 10 wherein at least one of the member rings of said fused, bicyclic heterocyclic ring moiety of said compound is substituted with one or more alkyl, aryl, alkoxy or hydroxy radicals.

13. The composition of claim 10 wherein said fused, bicyclic heterocyclic ring moiety of said compound is selected from the group consisting of 2,3,5,6-tetrahydrothiazolo[2,3-b]thiazol-7a-yl; 2,3-dihydrothiazolo[2,3-b]-thiazol-7a-yl; thiazolo[2,3-b]thiazol-7a-yl; 2,3,5,6-tetrahydrothiazolo[2,3-b]-(1,3)-thiazin-8a-yl; and 2,3,6,7-tetrahydro-(1,3)-thiazino[2,3-b]-(1,3)-thiazin-9a-yl.

14. The composition of claim 10 wherein $R^1$ is 2,3,5,6-tetrahydrothiazolo[2,3-b]thiazol-7a-yl.

15. The composition of claim 10 wherein said protozoa is Trichomonas vaginalis.

16. The composition of claim 10 wherein said compound is 5(6)-(2,3,5,6-tetrahydrothiazolo[2,3-b]thiazol-7a-ylthio)-2-carbomethoxyaminobenzimidazole.

17. The composition of claim 16 wherein said protozoa is Trichomonas vaginalis.

18. The composition of claim 10 wherein the hydrogen on the nitrogen at the 1-position is replaced with acyl having 1 to 6 carbon atoms, carbalkoxy having 2 to 7 carbon atoms, carbamoyl, or alkylcarbamoyl wherein the alkyl portion thereof has 1 to 4 carbon atoms.

* * * * *